(12) United States Patent
Marinozzi et al.

(10) Patent No.: US 9,360,460 B2
(45) Date of Patent: Jun. 7, 2016

(54) DEVICE FOR CALIBRATING AND TESTING ECHOTOMOGRAPHIC EQUIPMENT

(75) Inventors: Franco Marinozzi, Rome (IT); Fabiano Bini, Rome (IT)

(73) Assignee: UNIVERSITA DEGLI STUDI DI ROMA LA SAPIENZA, Roma (IT)

( * ) Notice: Subject to any disclaimer, the term of this patent is extended or adjusted under 35 U.S.C. 154(b) by 194 days.

(21) Appl. No.: 14/111,202

(22) PCT Filed: Apr. 11, 2012

(86) PCT No.: PCT/IB2012/051772
§ 371 (c)(1),
(2), (4) Date: Oct. 11, 2013

(87) PCT Pub. No.: WO2012/140582
PCT Pub. Date: Oct. 18, 2012

(65) Prior Publication Data
US 2014/0026634 A1    Jan. 30, 2014

(30) Foreign Application Priority Data
Apr. 12, 2011   (IT) .............................. RM2011A0185

(51) Int. Cl.
*G01N 29/30* (2006.01)
*A61B 8/06* (2006.01)
(Continued)

(52) U.S. Cl.
CPC ................ *G01N 29/30* (2013.01); *A61B 8/065* (2013.01); *A61B 8/08* (2013.01); *A61B 8/488* (2013.01); *A61B 8/587* (2013.01); *G09B 23/286* (2013.01)

(58) Field of Classification Search
CPC ..... G01N 29/30; G01N 29/28; G01N 29/348; A61B 5/02156; A61B 8/58

USPC ............. 73/1.83, 1.57, 1.67, 1.69, 1.82, 1.68, 73/595, 99, 119, 127, 597; 702/85; 600/463
See application file for complete search history.

(56) References Cited

U.S. PATENT DOCUMENTS

| | | | | |
|---|---|---|---|---|
| 4,894,013 A | * | 1/1990 | Smith ...................... | A61B 8/06 434/268 |
| 5,530,678 A | * | 6/1996 | Kosalos ................. | G01H 3/005 367/13 |
| 2010/0122566 A1 | * | 5/2010 | Kim ......................... | A61B 8/00 73/1.82 |

FOREIGN PATENT DOCUMENTS

| | | | | |
|---|---|---|---|---|
| CZ | GB 2434206 A | * | 7/2007 | ........... G01N 29/222 |
| GB | 2434206 A | | 7/2007 | |

(Continued)

OTHER PUBLICATIONS

Kanai H et al.:"A New Method to Measure Local Vibrations in a Heart Using Ultrasound", New Frontiers of Biomedical Engineering—Innovations From Nuclear Space Technology: 13th Annual International Conference of the Ieeeengineering in Medicine and Biology Society: Oct. 21-Nov. 3, 1991, ORlando Florida, USA; ISBN: 978-0/7808-0216-7.*

(Continued)

*Primary Examiner* — John Fitzgerald
*Assistant Examiner* — Jean Morello
(74) *Attorney, Agent, or Firm* — Volpe and Koenig, P.C.

(57) ABSTRACT

A device for calibrating and testing echotomographic equipment comprises an electric motor, a pair screw—female screw, wherein the screw is connected to an outlet shaft of the motor and the female screw is mobile with respect to a supporting plane, so as to transform a rotary motion of the motor shaft into a linear motion, a piston connected to the female screw and linearly mobile, coherently to the female screw, a membrane stressed by the piston, means apt to allow propagating ultrasound waves towards/from said membrane.

7 Claims, 2 Drawing Sheets

(51) Int. Cl.
*A61B 8/08* (2006.01)
*G09B 23/28* (2006.01)
*A61B 8/00* (2006.01)

(56) References Cited

FOREIGN PATENT DOCUMENTS

| GB | WO 2008093080 | A2 * | 8/2008 | ............... A61B 8/00 |
|----|---------------|------|--------|---------------------------|
| WO | 2008093080    | A2   | 8/2008 |                           |

OTHER PUBLICATIONS

Kanai H et al: "A New Method to Measure Local Vibrations in a Heart Using Ultrasound", New Frontiers of Biomedical Engineering—Innovations From Nuclear to Space Tehnology: 13th Annual International Conference of the Ieeeenginering in Medicine and Biology Society: Oct. 31-Nov. 3, 1991, Orlando, Florida, USA; Proceedings, Oct. 31, 1991, pp. 131-132, XP010102249, ISBN: 978-0-7803-0216-7.

* cited by examiner

DEVICE FOR CALIBRATING AND TESTING ECHOTOMOGRAPHIC EQUIPMENT

The present invention relates to a device for calibrating and testing diagnostic echotomographic equipment.

In the field of the clinical diagnosis the use of diagnostic survey systems based upon the Doppler effect is well known.

Such surveys are performed by means of the echotomographic equipment which, as known, is mainly constituted by a probe which transmits an ultrasound signal and receives the reflected Doppler wave the frequency thereof, due to the Doppler effect, is varied with respect to the transmitted one. Such probe is connected to an electronic system which, once received a return echo, performs a signal processing so as to make it visually representable onto a specific display system.

Such analyses can be applied in several fields of the medical diagnostics, according thereto the features of the echotomographic equipment and the type of the displayed results vary.

More specifically, in the field of the echocardiography, the Doppler analyses are used for evaluating cardiac pathologies, in particular various cardiac insufficiencies.

Among the used techniques, together with the traditional systems based upon the echo signal generated by the hematic flows, in the last years even systems have been developed utilizing the Doppler effect to detect and study the motion of the cardiac muscle.

Such analysis technique, generally known with the name of tissue Doppler analysis or Tissue Doppler Imaging (TDI), analyses the echoes coming from the myocardial fibres which generate a Doppler signal with low frequency (in the order of kilohertzs) and relatively high width.

The results of such analyses are represented by a graph reproducing the course of the mitral ring speed.

The diagnosis is then performed by analysing the profile detected during the clinical examination and compared by the Physician to the values and the physiological, both normal and pathological, courses known to him/her.

In greater detail, the tissue Doppler analysis measures the peak speeds of the cardiac tissues during the so-called protodiastolic and telediastolic waves, by allowing to distinguish a normal profile of the instantaneous speeds of the mitral valve from the one associated to cardiac dysfunctions.

Therefore, it results clear that, being such analyses based upon a comparative survey, in order to guarantee a correct operation of the echotomographic equipment, it is necessary that this is calibrated and the performances thereof are periodically checked. Such checks are currently performed by using a test object, normally called phantom, thereon the device is used so as to obtain a test signal.

In case of the Doppler analyses, the phantom can be constituted by a disc rotating with constant speed dipped into a basin containing water. The application of the probe of the echotomographic equipment onto the phantom allows receiving test signals in order to check the response correctness of the same.

Alternatively, the use of a piston has been proposed, driven by a hydraulic system, fed by a stepping motor, able to generate sinusoidal cycles with constant frequency, the width thereof reproduces the peak of maximum speed reached by the protodiastolic wave.

However, the main limit of such testing systems consists in that they are not able to simulate the real motion of the cardiac tissue, but they limit to provide test signals which do not reproduce the real speed profiles of the tissues object of the survey. Obviously, this does not allow the comparison to the real measurements.

The U.S. Pat. No. 4,894,013 describes a device for calibrating and testing echotomographic equipment wherein the cardiac tissue is simulated by a membrane, but the position of this membrane cannot be checked.

Therefore, the technical problem underlying the present invention is to provide a device for testing and checking echotomographic equipment allowing to obviate the drawbacks mentioned above with reference to the known art.

Such problem is solved by the device for calibrating and testing diagnostic echotomographic equipment according to claim 1.

The invention mentioned previously has then some important advantages; first of all that of allowing to reproduce shifting and speed profiles inside a much wider field than the pre-existing devices, in particular it is possible reproducing motions analogous to those of the cardiac tissue, so as to obtain reference profiles which could be used for a calibration and subsequent operation check of echotomographic equipment, as well as with search purposes.

Other advantages, features and use modes of the present invention will result evident from the following detailed description of some embodiments, shown by way of example and not with limitative purposes. The figures of the enclosed drawings will be referred to, wherein.

Figure 1:
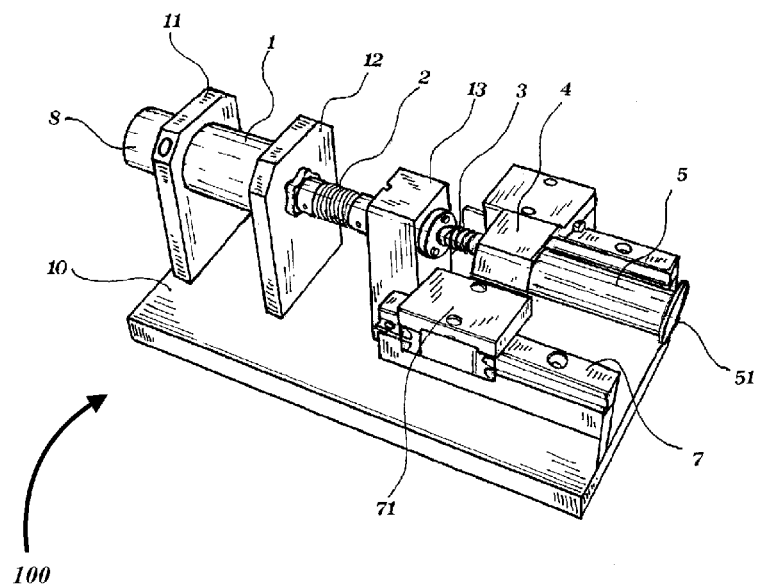
FIG. 1 is a perspective view of the device according to the present invention.
Figure 2:
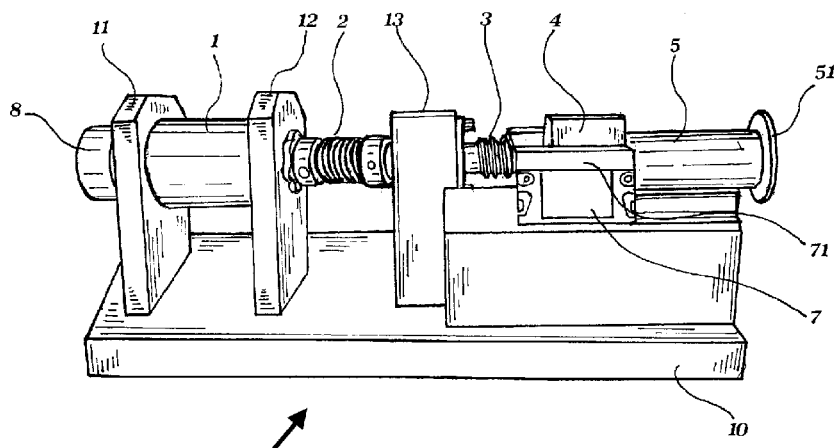
FIG. 2 is a side view of the device of FIG. 1.

By firstly referring to FIG. 1, a device for calibrating and testing echotomographic equipment is designated as a whole with the reference number 100.

The device 100 is formed by a supporting base 10, which identifies a reference plane, whereupon an electric motor 1 is fastened by means of a pair of supports 11, 12.

Figure 3:
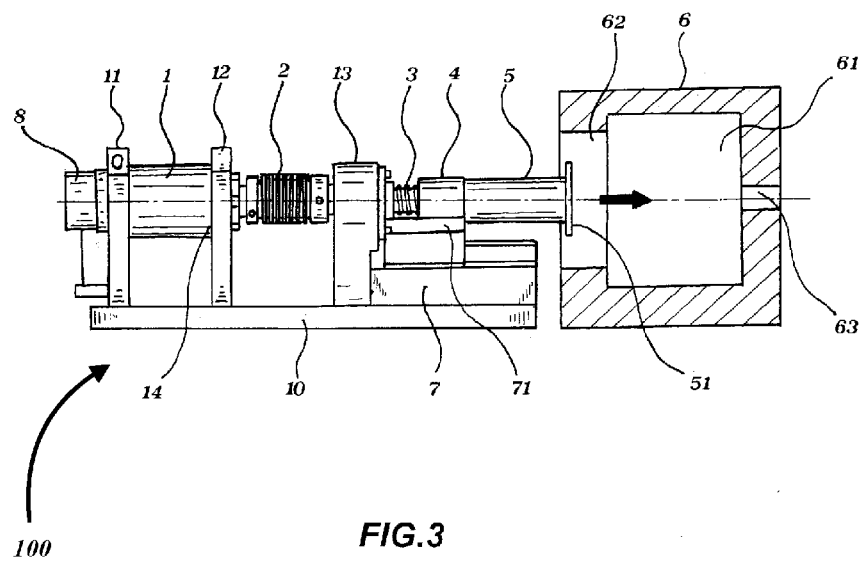
FIG. 3 is a schematic side view of the device according to the present invention associated to means for propagating waves.

The electric motor 1, for example a direct current motor with permanent magnets, has a shaft 14, schematically illustrated in FIG. 3, which is fit, on one side, together with an incremental encoder 8, to detect the angular speed of the motor and, on the other side, with an elastic joint 2, which, in turn, transmits the rotary motion of the motor 1 to a screw 3.

The device 100 has an additional support 13 at the connection between joint 2 and screw 3, wherein there is a roller bearing, not illustrated in figure.

Since, as it will be seen in greater detail hereinafter, the motor is subjected to relevant accelerations caused in particular by the quick and frequent rotation inversions during the device operation, the elastic joint 2 allows protecting the bearing supporting the screw 3 from radial and axial overloads respectively caused by axial misalignments and slidings.

The screw 3 is then coupled to a female screw 4, free to move with respect to the supporting plane 10 of the device. More precisely, the female screw 4 is fastened to a pair of sliding shoes 71, sliding along a direction y above rails 7 fastened to the base 10.

In this way, the rotation of the female screw 4 is prevented, even if allowing the linear motion thereof along the direction Y.

Consequently, the rotation of the screw 3 produces a corresponding linear motion of the female screw 4 along such direction.

Furthermore, the rails 7 can even be equipped with an additional position sensor, apart from the encoder, such as for example a linear variable differential transformer (LVDT), not shown in the drawings.

A piston 5, formed by a hollow cylindrical body with an enlarged end 51 shaped like a disc, is further fastened to the female screw 4.

In this way, the screw 3 could be housed inside the hollow body during the motion of the female screw 4.

Therefore, the piston 5 too could move with linear motion together with the female screw 4, controlled by the rotation of the motor 1.

Such motion is then transmitted by means of the enlarged end 51 to a membrane 62, which is stressed by the shifting of the piston 5.

More precisely, and as illustrated in FIG. 3, the membrane 52 is fastened to a container 6 and, in particular, it forms a wall thereof. The container 6 has a hollow portion 61, inside thereof there is a liquid, specifically distilled water. Obviously, other types of liquids or solidified gel can be used, such as for example, milk, castor-oil and agarose gel apt to reproduce the acoustic features of biological fluids. Furthermore, in addition to the hollow container filled up with liquid, the membrane 62 can be associated even to other elements, such as for example portions of biological tissue and/or materials which simulate the features thereof as far as the reflection of ultrasounds is concerned.

Figure 4:
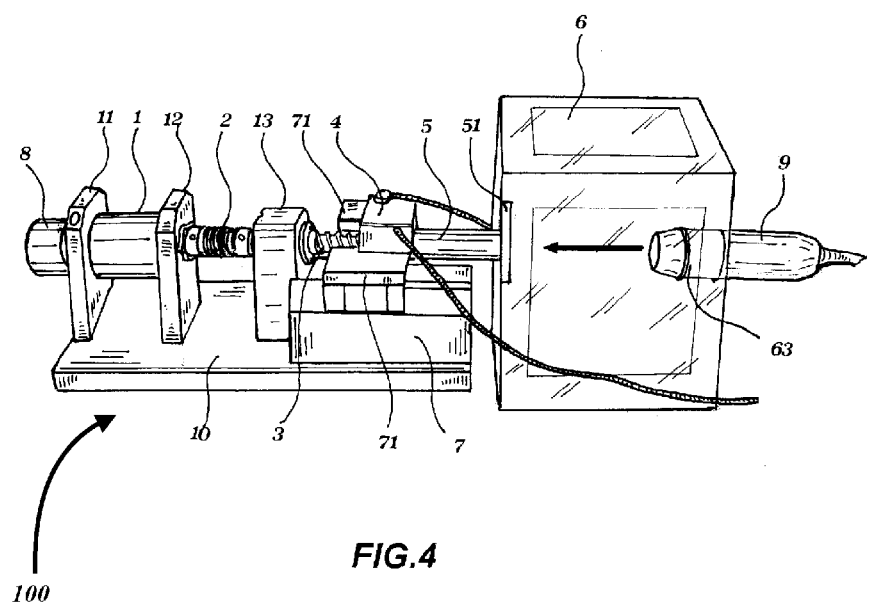
FIG. 4 is a side view of the device of FIG. 3 during the use of echotomographic equipment.

The calibrating and checking operation of echotomographic equipment, described in FIG. 4, provides the positioning of the probe 9 of the echotomographic equipment at one contact wall 63 of the container, so as to transmit a series of ultrasound waves towards the membrane 62.

The alternating motion of the piston, generated by a rotation with variable speed of the motor 1, produces a shifting of the membrane 62 which, when it is struck by ultrasound waves generated by the probe 9, generates a reflected wave which propagates by means of the liquid in the container 6 until reaching the wall 63 wherein it will be detected by the probe 9 itself.

The device further comprises a control system of the motor 1, not represented in figure, which allows controlling the rotation of the motor based upon predetermined speed and acceleration values. In this way, a predetermined motion could be given to the piston, which motion will produce on the membrane 62 a shifting profile apt to reproduce the one of the cardiac tissue.

The calibration and check of the echotomographic equipment could be performed by giving a known reference motion to the piston and by comparing the reading of the instrument to be calibrated to a—already known—reference shifting profile associated to such motion of the piston. The possibility of using a profile analogous to those obtainable during the real use of the medical instrument allows calibrating and checking the operation of the same for the specific application thereto it is destined, thus guaranteeing a maximum accuracy in the results.

The invention solves thus the proposed problem, allowing to obtain a test profile of any feature. In particular, the motion of the electric motor could be set so as to obtain a profile wholly similar to the reference one, corresponding to normal values. Analogously, the device can reproduce profiles testifying the occurrence of pathological conditions.

The invention claimed is:

1. A device for calibrating and testing echotomographic equipment comprising:
    an electric motor;
    a pair screw—female screw, said screw being connected to an outlet shaft of the motor and said female screw being mobile with respect to a supporting plane, so as to transform a rotary motion of the shaft of the motor into a linear motion;
    a piston connected to said female screw and linearly mobile, coherently to said female screw;
    a membrane stressed by said piston;
    means for allowing propagation of ultrasound waves towards/from said membrane, and
    means for detecting a linear position of said female screw and piston.

2. The device according to claim 1, wherein said screw is connected to said shaft by means of an elastic joint.

3. The device according to claim 1, further comprising means for detecting an angular speed of said motor.

4. The device according to claim 1, wherein said female screw is supported by at least a guide thereto a sliding shoe, connected to said female screw, is slidingly associated.

5. The device according to claim 1, wherein said piston has a hollow cylindrical body and an enlarged end adapted to come into contact with said membrane.

6. The device according to claim 1, wherein said means for allowing the propagation of ultrasonic waves comprises a hollow container, a wall thereof being formed by said membrane.

7. The device according to claim 6, wherein said container is filled up with liquid, said membrane being in contact with the liquid.

* * * * *